United States Patent [19]

Lawrence et al.

[11] Patent Number: 5,661,305

[45] Date of Patent: Aug. 26, 1997

[54] METHOD FOR MONITORING ABSORBED DOSE IN AN ELECTRON BEAM

[75] Inventors: Courtlandt B. Lawrence; Joseph McKeown, both of Kanata, Canada

[73] Assignee: Atomic Energy of Canada Limited/Energie Atomique du Canada Limitee., Ontario, Canada

[21] Appl. No.: 565,150

[22] Filed: Nov. 30, 1995

[30] Foreign Application Priority Data

Sep. 29, 1995 [CA] Canada ................................. 2159531

[51] Int. Cl.⁶ ............................................ H01J 37/30
[52] U.S. Cl. ............................ 250/397; 250/492.3
[58] Field of Search ........................ 250/397, 398, 250/400, 492.1, 492.3, 455.11, 453.11

[56] References Cited

U.S. PATENT DOCUMENTS

| | | | |
|---|---|---|---|
| 3,188,469 | 6/1965 | Eukel . | |
| 3,733,546 | 5/1973 | Faltens et al. | 324/71 R |
| 4,233,515 | 11/1980 | Dietrich et al. | 250/397 |
| 4,290,012 | 9/1981 | Berte et al. | 324/71 EB |
| 4,336,597 | 6/1982 | Okubo et al. | 364/560 |
| 4,427,890 | 1/1984 | Taumann | 250/397 |
| 4,629,975 | 12/1986 | Fiorito et al. | 324/71.3 |
| 4,751,393 | 6/1988 | Corey, Jr. et al. | 250/397 |
| 5,177,367 | 1/1993 | Suzuki | 250/492.3 |
| 5,198,676 | 3/1993 | Beneviste et al. | 250/397 |
| 5,307,396 | 4/1994 | Tsuchino | 378/146 |
| 5,449,916 | 9/1995 | Smyth et al. | 250/492.3 |

FOREIGN PATENT DOCUMENTS 2247736  10/1974  France .

OTHER PUBLICATIONS

Derwent Publications, Ltd., London, GB, Database WPI, Section EI, Week 8318, Class S03, AN 83–F9991K & SU,A,830 888 (Tomsk Poly), 15 Sep. 1982.

Primary Examiner—Jack I. Berman
Assistant Examiner—Kiet T. Nguyen
Attorney, Agent, or Firm—Sughrue, Mion, Zinn, Macpeak & Seas

[57] ABSTRACT

Absorbed dose in a product being irradiated by an electron beam is determined by measuring the collectable current in a beam stop and correlating the current to absorbed dose.

7 Claims, 7 Drawing Sheets

METHOD FOR MONITORING ABSORBED DOSE IN AN ELECTRON BEAM

FIELD OF THE INVENTION

This invention relates to a method for determining the absorbed dose of a product irradiated with an electron beam by measuring the electrical charge collected on an electron beam stop.

BACKGROUND OF THE INVENTION

Electron beam accelerators are used to irradiate products with a beam of electrons. This form of irradiation has a number of useful applications. Medical products such as sutures, syringes, gloves, and other packaged items can be sterilized by this means. Electron beam irradiation can pasteurize and sterilize food products as well as de-infest them of insects and parasites. Electron beam irradiation can also be used to alter material properties such as the polymerization, curing or enhancing of polymers, plastics and cellulose.

The electron beam accelerators used for these applications are high power accelerators. The current industry standard is to employ an accelerator having a beam energy of 10 MeV. The depth of penetration of the electron beam is proportional to the electron beam energy and the density of the product. As a result, the surface density of the product must be limited to approximately 3.5 $g/cm^2$ for single sided radiation and approximately 8 $g/cm^2$ for a product being irradiated from opposite sides.

When sterilizing and pasteurizing products, it is essential that the electron beam sufficiently penetrate the product in order that it deliver the prescribed radiation dose to all areas of the product being irradiated. Correspondingly, there must also be an effective means to measure the absorbed dose to ensure that adequate irradiation has taken place.

The current practice used to measure absorbed dose is to qualify a particular product for electron beam irradiation in order to establish the efficacy of the irradiation process on that product. The absorbed dose is measured by plating film dosimeters at various locations throughout the product, irradiating the product and then reading the dosimeters and tabulating the dose at each dosimeter location. The radiochromic dosimeters acquire an optical density in proportion to the radiation dose that they receive from the electron beam. From the tabulations of minimum and maximum dose, the nominal dose is established and the packing and orientation of the product is then specified to achieve the required dose. By this method, the qualification of each product creates a recipe for irradiation of that product. For the routine irradiation of subsequent production quantities, quality assurance procedures are followed to ensure that the recipe is followed. One commonly adopted quality assurance procedure is to place a dosimeter on the outside of a sample product box to confirm that the box passed through the electron beam. The placement of dosimeters inside product boxes prior to the irradiation process is precluded because retrieval of the dosimeters after irradiation would recontaminate the product.

There are a number of drawbacks to the method currently being used. For instance, if the product is incorrectly loaded on the irradiation conveyor or tray (for example it may be placed on its edge instead of on its bottom), the irradiation may be ineffective if the exposed surface of the product has too great a surface density to allow penetration of the product. Ineffective irradiation caused by incorrect loading is difficult to detect with dosimeters placed on the outside of product packages. Further, as it is impractical to place dosimeters on the outside of each and every product package, there is no assurance that a product not tested has been adequately irradiated.

Another potential problem arises when product manufacturers either deliberately or inadvertently repackage products or vary the composition of the product without informing the operator of the irradiation service centre. The operator is not normally permitted to open the manufacturers' boxes, and will thus fail to recognize that the new product either requires a new irradiation recipe or that it cannot be properly irradiated. For example, if an irradiation service centre qualifies the sterilization of a box of rubber gloves and the glove manufacturer subsequently discovers a way to compress the gloves and package more gloves into each box, without informing the service centre operator, the new box may be too dense to be penetrated by the electron beam. Irradiation would be ineffective and the problem would go unnoticed.

Another disadvantage to the use of film dosimeters to detect absorbed dose is that they may not detect malfunctioning of the accelerator. It is possible that, through malfunction, the energy of the accelerator may change during irradiation of product. Accelerators which are able to accurately monitor their energy will shut down and avoid improper treatment of product, however, other accelerators rely on periodic calibration to verify beam energy. Thus, depending on the time between calibrations, a significant quantity of product may have to be held in quarantine until the energy is verified. If the energy is found to be out of tolerance, significant amounts of product may need to be discarded.

Thus there is a need for a more accurate and reliable method for instantaneously assessing the radiation dose absorbed by a product to ensure that it has been properly irradiated.

SUMMARY OF THE INVENTION

Products can be irradiated by positioning them in the path of an electron beam generated by an electron beam accelerator. High power electron accelerators require a beam stop at the output of the accelerator to stop the electron beam and absorb the charge that it deposits. During product irradiation, such a beam stop will receive the collected charge, i.e. the charge that is not deposited in the product. The absorbed dose of the product can be determined by correlation with the collected charge. A graphical representation showing the product's absorbed dose can be produced. These graphical representations are useful as a comparative tool for quality assurance purposes.

Thus in accordance with one aspect of the present invention, there is provided a method for determining absorbed dose of a product disposed in the path of an electron beam comprising: providing an electron beam source; providing an electron beam stop in the path of said beam effective to absorb electrons incident thereon and generate an output proportional to the collected charge induced therein by said incident electrons; placing said product in the path of said electron beam between said source and said beam stop; measuring the collected charge in said beam stop; and correlating said measured collected charge to absorbed dose.

In accordance with another aspect of the present invention there is provided the above method for determining absorbed dose of a product disposed in the path of an electron beam wherein the step of correlating the measured collected charge to the absorbed dose comprises: obtaining charge deposition distribution values as a function of depth of a sample of said product; obtaining dose deposition distribution values as a function of depth of said sample; integrating said charge and dose deposition distribution values over the maximum depth of the product through which said beam can pass to obtain integrated charge deposition values and absorbed dose deposition values respectively; subtracting said integrated charge deposition values from the total charge induced in said beam stop per incident electron in the absence of said product to obtain collected charge in said beam stop as a function of depth of said sample; correlating said absorbed dose deposition values as a function of said collected charge distribution values; obtaining from said correlation the absorbed dose deposition value associated with the measured collected charge.

In accordance with another aspect of the present invention there is provided a method for determining whether a product irradiated by an electron beam has acquired a predetermined absorbed dose comprising: determining absorbed dose of the product in accordance with the methods described above; comparing said determined absorbed dose to said predetermined absorbed dose; and rejecting said product if said determined absorbed dose is less than said predetermined absorbed dose.

In accordance with another aspect of the present invention there is provided a method for determining whether a product disposed in the path of an electron beam has absorbed a predetermined dose comprising: providing an electron beam source; providing an electron beam stop in the path of said beam effective to absorb electrons incident thereon and generate an output proportional to the collected charge induced therein by said incident electrons; determining the collected charge induced in said beam stop when a sample of said product has absorbed said predetermined dose; placing said product in the path of said electron beam between said source and said beam stop; measuring the collected charge in said beam stop; and rejecting said product if said measured collected charge exceeds said determined collected charge.

In accordance with another aspect of the present invention there is provided a method for monitoring the absorbed dose of a product moving through a scanned electron beam at right angles to said scanned electron beam as a function of time and beam position comprising; providing an electron beam source; providing an electron beam stop in the path of said beam effective to absorb electrons incident thereon and generate an output proportional to the collected charge induced therein by said incident electrons; moving a representative sample of said product through the path of said electron beam between said source and said beam stop; measuring the collected charge in said beam stop for said representative sample at predetermined values of time and beam position; correlating said measured collected charge for said representative sample to absorbed dose for said representative sample to determine absorbed dose of said representative sample as a function of time and beam position; moving said product through the path of said scanned electron beam; measuring the collected charge in said beam stop at predetermined values of time and beam position for said product; correlating said measured collected charge for said product to absorbed dose for said product to determine absorbed dose as a function of time and beam position; comparing the absorbed dose as a function of time and beam position for said representative sample to the absorbed dose as a function of time and beam position for said product to determine the presence of predetermined levels of difference therebetween.

BRIEF DESCRIPTION OF THE DRAWINGS

These and other features of the present invention are more fully set forth below in the accompanying detailed description, presented solely for purposes of exemplification and not by way of limitation, and in the accompanying drawings, of which.

DETAILED DESCRIPTION OF THE PREFERRED EMBODIMENT

When irradiating products with an electron beam, it is often necessary to be able to determine the radiation dose absorbed by each product. In the present invention, absorbed dose is correlated to the electrical charge which passes through the irradiated product. Thus absorbed dose can be accurately determined by measuring the charge collected on a beam stop and determining the absorbed dose which correlates to that charge. The correlation is done by ascertaining the depth-dose and depth-charge distribution curves for any given product, measuring the total charge of the electron beam, and computing this data to obtain integrated dose, integrated charge and collected charge. The correlation of dose as a function of collected charge is then produced.

Thus, as a first step in the correlation, the depth-dose and depth-charge distribution curves which correspond to the composition of the product must be ascertained. When a fast moving electron passes through a medium it encounters a large number of interactions that result in dispersion and loss of kinetic energy of the electron. The statistical nature of the interaction process results in finite distribution of the charge and energy deposition along the depth of the interacting medium.

The depth-dose and depth-charge distribution curves for an elemental material can be determined by a number of methods. For instance, the dose can be measured directly by using radiation sensitive film inserted between layers of the product. After the product film assembly has been exposed to the electron beam for a suitable mount of time, the films acquire an optical density proportional to the dose of each layer. By individually weighing the layers, the dose versus depth in $g/cm^2$ can be tabulated. The same information can be obtained by placing a single portion of film between two wedges of the product arranged with the thin edge of one wedge above the thick edge of the other wedge. Similarly, deposited charge can be measured by placing insulating material between layers of a conducting material and measuring the charge of each layer. The relationships between dose and depth and charge and depth can also be estimated by computer modelling techniques and in particular, by the use of Monte Carlo codes which estimate the conduct of individual electrons travelling through a particular product.

Depth-dose and depth-charge distributions for a number of elemental materials have been tabulated and published in "Tables of Charge- and Energy-Deposition Distributions in Elemental Materials Irradiated by Plane-Parallel Electron Beams with Energies between 0.1 and 100 MeV", by P. Andreo, R. Ito and T. Tabata, Research Institute for Advanced Science and Technology, University of Osaka Prefecture, Technical Report No. 1, April 1992. The term absorbed dose is commonly used by those skilled in the art to describe deposited energy and is used in that manner herein.

Figure 1:
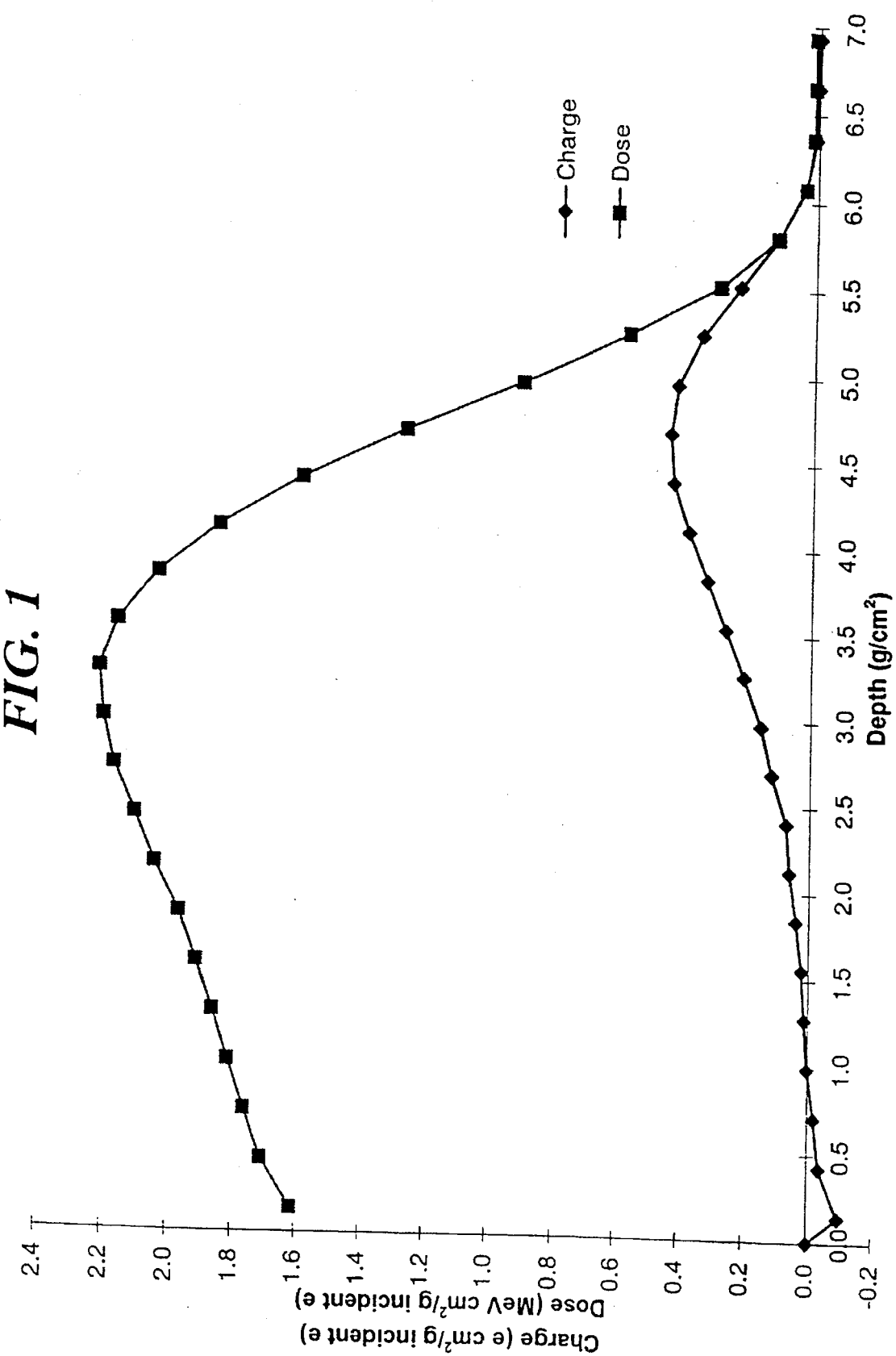
FIG. 1 is a graphical representation of the dose and charge versus depth distribution for 10 MeV electrons in carbon.

By way of example, FIG. 1 shows the charge and dose distributions as a function of depth for carbon. This graph has been produced by plotting the relevant values published in the article by Andreo et al. Similar graphs can be produced for other elemental materials by employing any one of the methods referred to above.

Figure 2:
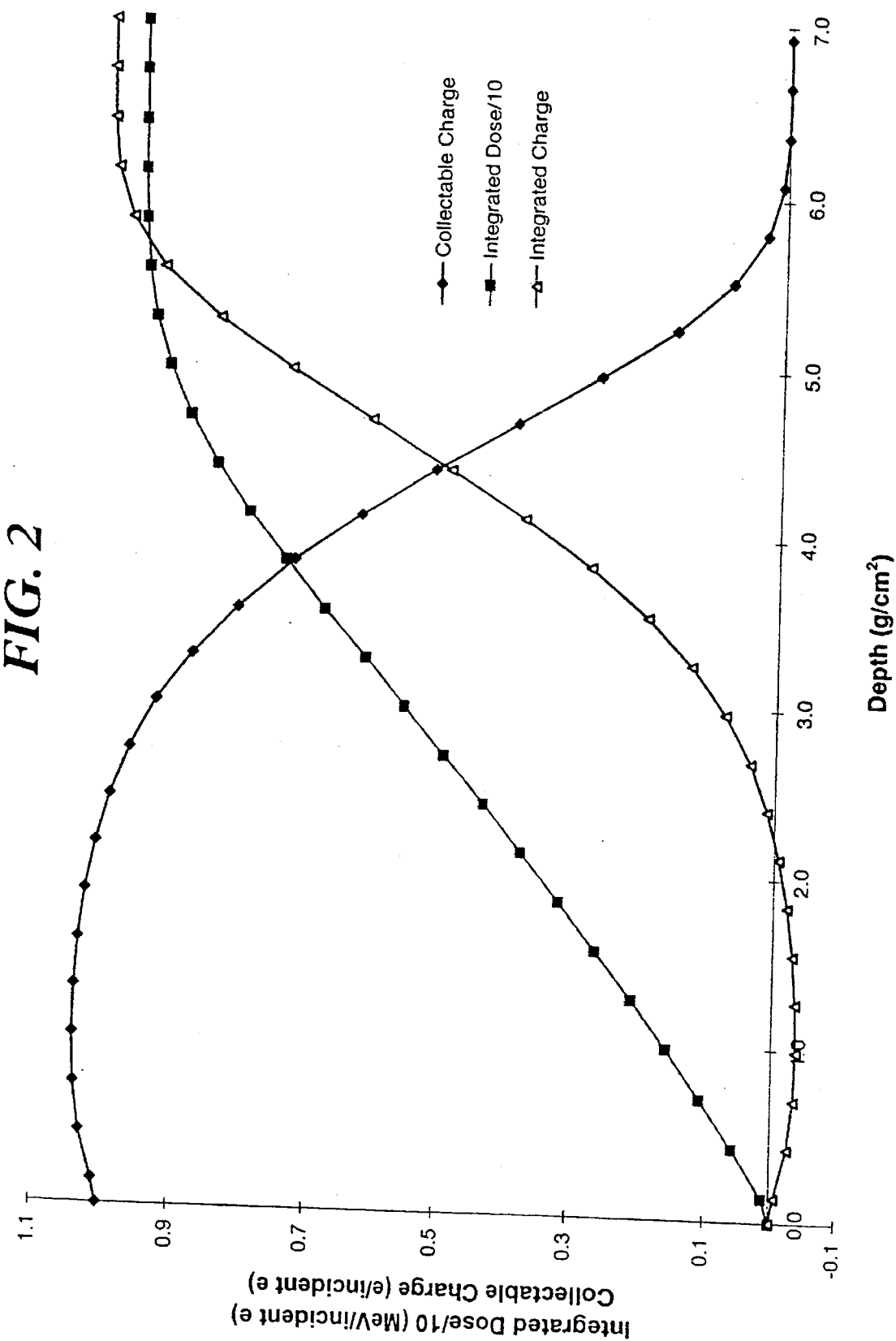
FIG. 2 is a graphical representation of integrated dose, integrated charge and collected charge versus depth distribution for 10 MeV electrons in carbon.

Once the depth-dose and depth-charge distributions have been ascertained, integrated dose, integrated charge and collected charge can be computed. FIG. 2 shows integrated dose, integrated charge and collected charge as a function of depth for carbon. Integrated dose is calculated by integrating the deposited dose versus depth curve shown in FIG. 1 and similarly, integrated charge is calculated by integrating the deposited charge versus depth curve shown in FIG. 1. The collected charge curve is the charge that is not trapped in the product and can therefore be collected on the side of the product opposite to the incident beam. This curve has been calculated by subtracting the integrated charge versus depth from the total charge. Thus, as the collected charge curve shows, for a product with zero thickness the collected charge is one electron per incident electron. For a very thick product the collected charge is zero.

Figure 3:
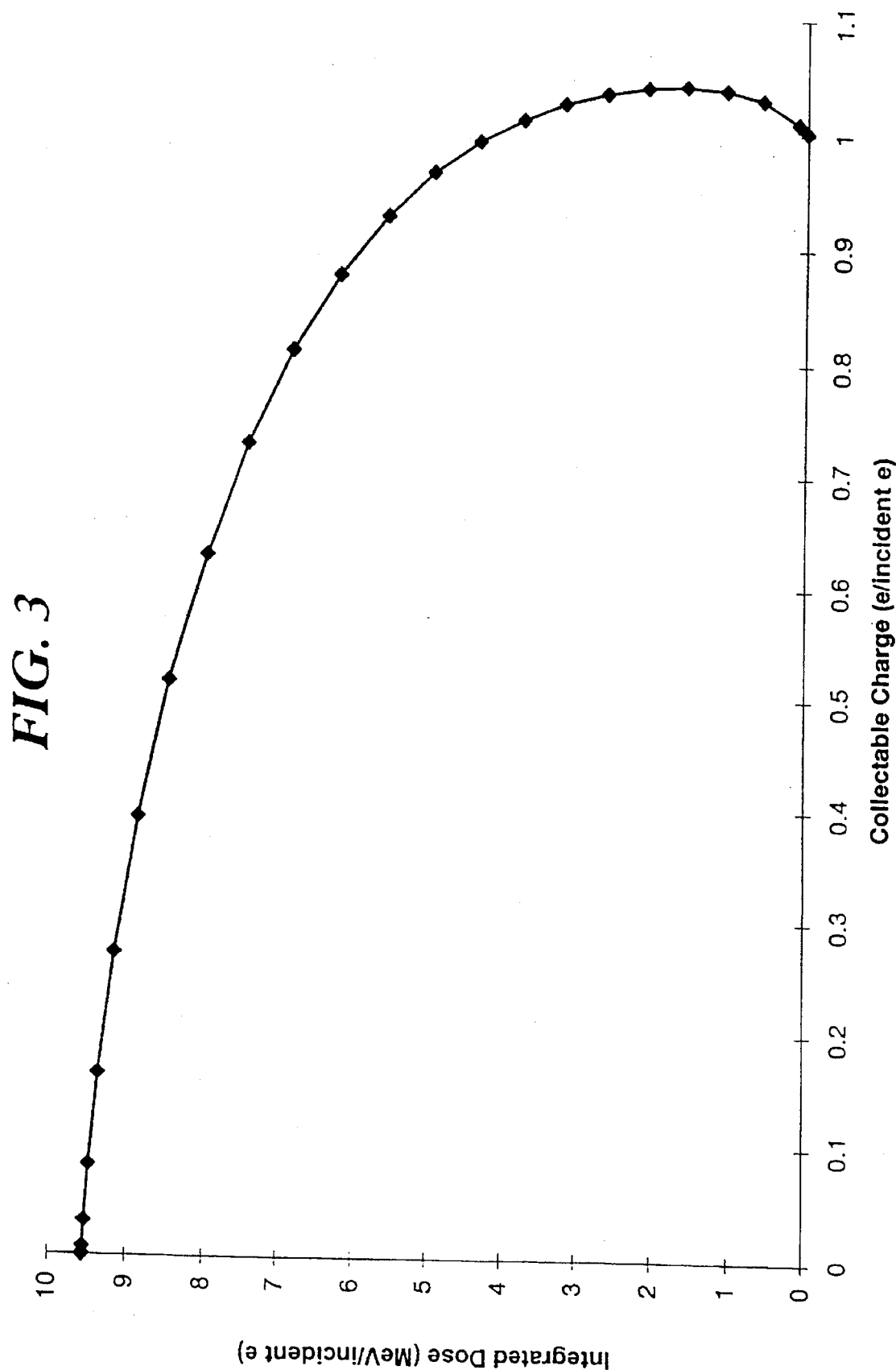
FIG. 3 is a graphical representation of the integrated dose versus collected charge for 10 MeV electrons in carbon.

With reference now to FIG. 3, integrated dose as a function of collected charge is obtained by replotting the data shown in FIG. 2. The curve in FIG. 3 thus represents the relationship between the collected charge of a beam stop and the absorbed dose of an irradiated product for products composed principally of carbon.

The integrated dose versus collected charge curve can also be plotted by taking the measurements directly. In such a case, samples of differing thickness of a product are passed through the electron beam. Film dosimeters placed in or on the product indicate the dose received by that sample. The collected charge on the beam stop for each sample can be measured and then correlated with the dose.

Figure 4:
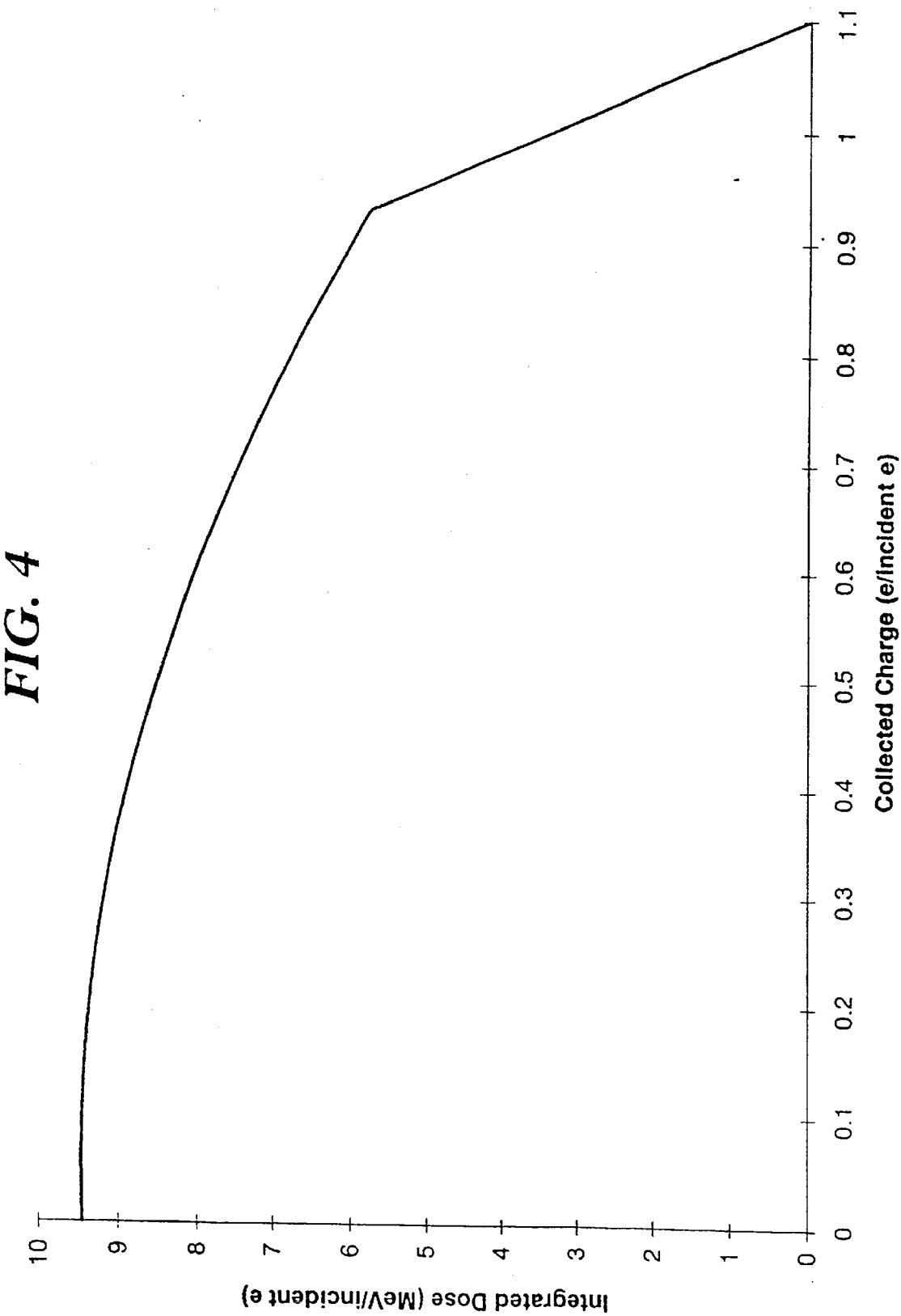
FIG. 4 is a modified graphical representation of the integrated dose versus collected charge for 10 MeV electrons in carbon.

In practice, it may be necessary to modify the FIG. 3 curve because in the area directly above 1 e/incident e, the curve is double valued. To overcome this problem the curve above 0.925 e/incident e has been approximated to a straight line that joins the curve at 0.925 and passes through 1.1. If the correlation will be conducted by computer program, the curve below 0.925 is fitted to a second order polynomial to minimize computation time. The resultant curve is shown in FIG. 4. Thus, below 0.925 the collected charge can be related directly to absorbed dose, but above 0.925 the collected charge is simply a signature to provide comparative information. As the area below 0.925 represents about 60% of dose being absorbed, this is representative of the amount of dose which is of practical use in sterilizing and pasteurizing and thus represents the most important part of the curve.

From the data in FIG. 3 or FIG. 4, the absorbed dose can be determined based on the current (charge per unit time) which is collected in the beam stop.

Figure 5:
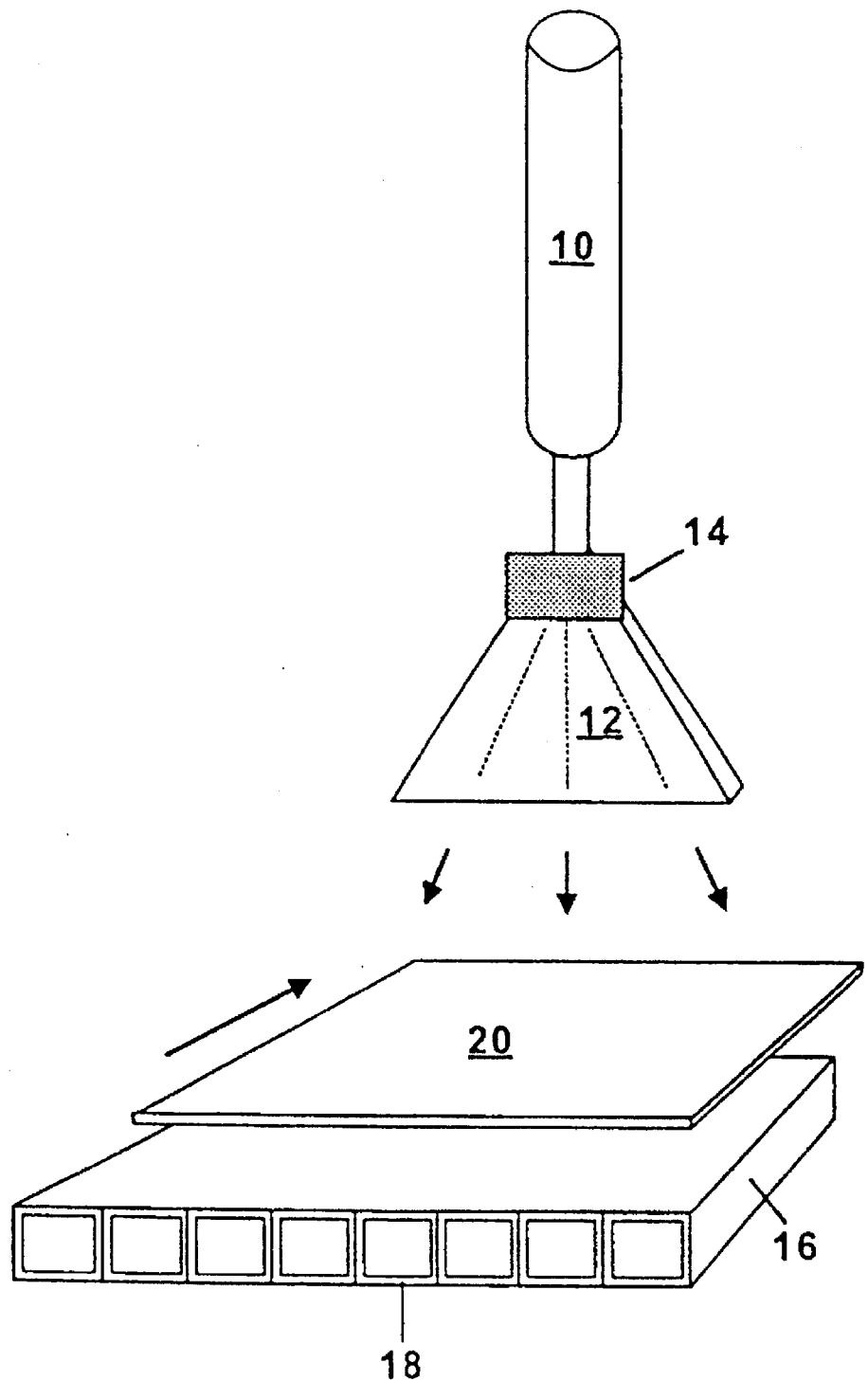
FIG. 5 is perspective view of an electron beam accelerator, a conveyor and a beam stop for use in the present invention.

Referring now to FIG. 5, an example of an apparatus used to carry out the present invention is shown. Accelerator 10 generates an electron beam that is scanned through scan horn 12 by scan magnet 14. Electron beam stop 16 is used in association with accelerator 10. Cooling water is pumped through channels 18 in the beam stop to prevent overheating. Any beam stop which is suitable for use with a high power electron beam accelerator and which can measure current can be used to practice this invention. Conveyor 20 operates to advance trays (not shown) in the direction of the arrow through the path of an electron beam from accelerator 10.

In accordance with the present invention, a graphical representation indicating the spatial distribution of absorbed dose can be displayed in the form of a signature map. To produce a signature map, it is necessary to obtain data with respect to time (corresponding to conveyor travel) and beam position in addition to measuring the collected current. Time is computed from the sampling frequency. The beam position is determined by measuring the scan angle. An electron beam is scanned by a varying magnetic field in the accelerator's scan magnet. The current in the scan magnet provides a measure of the instantaneous scan angle since the magnetic field is proportional to current. Some electronic filtering of the current signal may be required to compensate for the delays in the magnet due to hysteresis and eddy current losses. An alternative technique is to measure scan angle by placing a hall-effect magnetic field probe in the scan magnet. However, as hall probes are prone to rapidly deteriorate in the ionizing radiation field around an accelerator, it is necessary to protect them by a radiation shield or replace them frequently. The scan position and collected current data are read into a digital computer with a high speed analog-to-digital converter that is synchronized to the pulses from accelerator 10.

Figure 6:
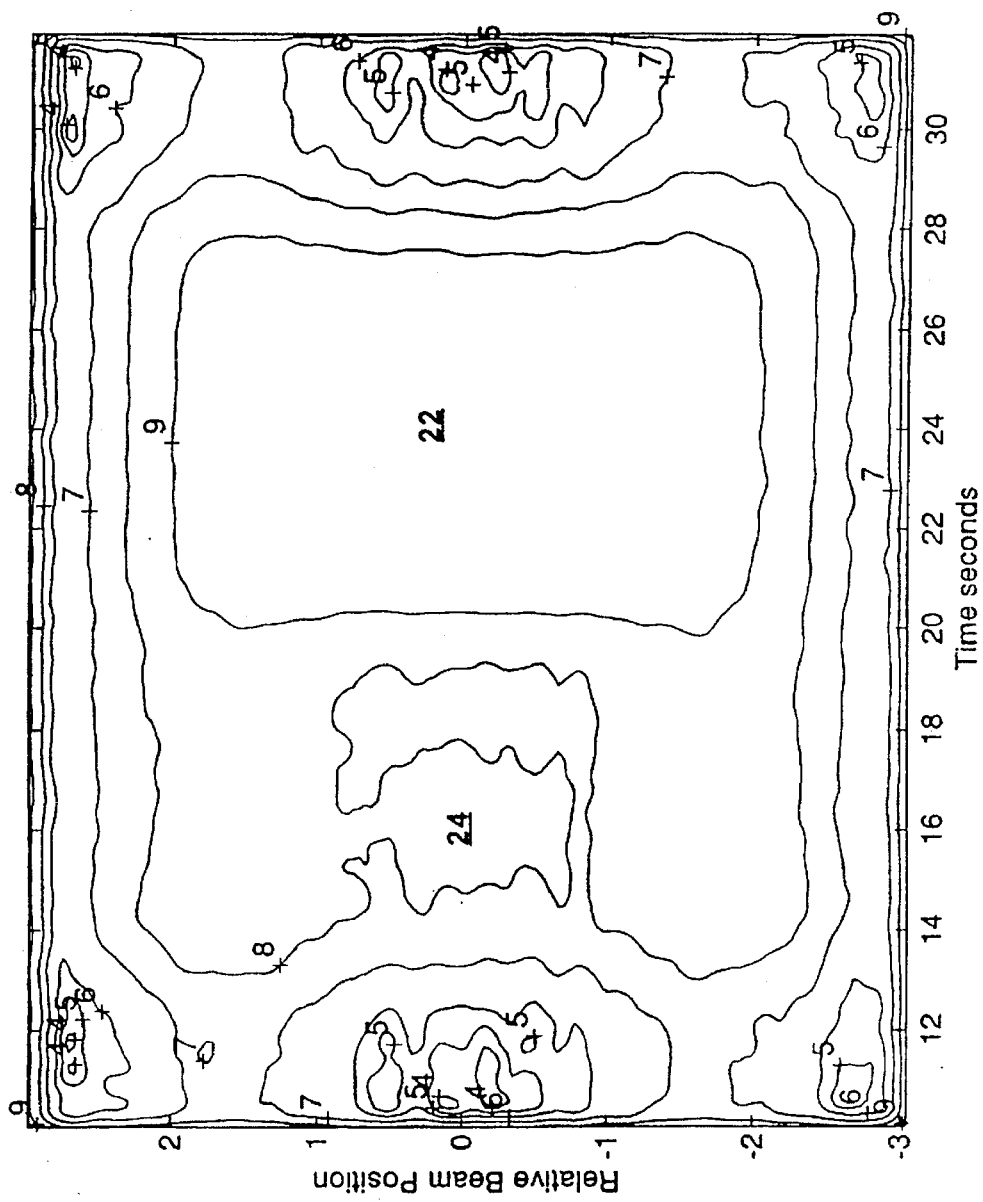
FIG. 6 is a graphical representation of absorbed dose as a function of time and beam position for a stack of pulp and a calorimeter on a tray.

FIG. 6 is an example of a graphical representation which has been generated by a computer program and which shows the absorbed dose of a tray containing a stack of pulp and a circular calorimeter. In this example, the x-axis indicates time, the y-axis indicates beam position, and the contour lines represent absorbed dose. The numbers on the contour lines represent MeV per incident electron. The stack of pulp is represented by the rectangle generally designated by numeral 22. The absorbed dose value of 9 MeV allocated to rectangle 22 signifies that the stack of pulp has absorbed near maximum dose. The product signature for the stack of pulp also shows good uniformity of penetration. The calorimeter is represented by the irregular shaped contour which is generally designated by numeral 24. The absorbed dose of the calorimeter with the tray is 8 MeV, slightly less than the stack of pulp. In this example, the stack of pulp was selected such that the surface dose and the dose at the bottom are the same. The tray used in this example is ¼ inch thick aluminum. If the tray was made of thinner material or was partially transparent, then up to ½ of the incident charge would be collected by beam stop 16. Detail of the dose absorbed by the product can be enhanced by using a tray which absorbs less of the charge that passes through the product. This can be achieved by constructing the tray of expanded or perforated metal. The resolution shown in FIG. 6 is limited by the diameter of the electron beam as it strikes the absorbing material. For the example shown, the spot diameter is about 20 cm and therefore features of the tray and supporting conveyor are smeared over that area.

Figure 7:
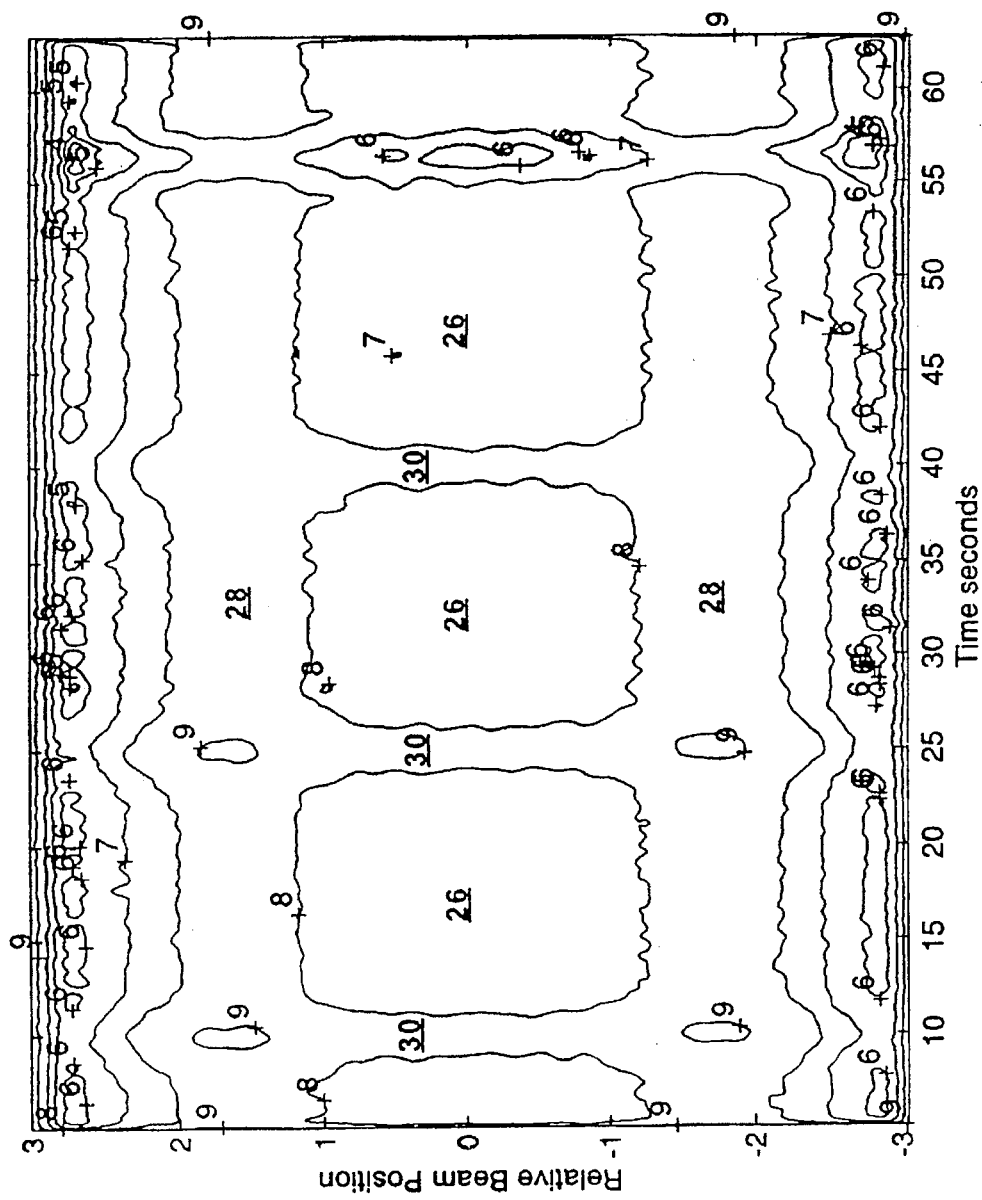
FIG. 7 is a graphical representation of absorbed dose as a function of time and beam position for empty trays.

FIG. 7 is an example of a graphical representation of the absorbed dose of empty trays. The large rectangles in the centre of the signature, generally designated by the numeral 26, represent the tray bottoms. The areas above and below tray bottoms, generally designated by the numeral 28, represent the conveyor and tray supports. The vertical areas 30 between the tray bottom represent the edges of the trays that have been strengthened with additional aluminum.

It is also possible to display a graphical representation of the collected charge in the beam stop for a product irradiation. The time, collected charge and beam position data are collected and displayed in a format similar to the signatures for absorbed dose.

The signature maps for absorbed dose and collected charge can be used in a quality assurance context to monitor the irradiation of a quantity of similar product. This form of monitoring is carried out at an irradiation service centre and has particular utility in sterilizing products such as medical equipment. Before irradiation of a product is commenced at a service centre, it is recommended that the electron beam is qualified in the absence of product to ensure that the electron energy, current, scan width and scan uniformity are within prescribed limits. Qualification of the electron beam can be done by any one of a number of known methods. A signature map for the qualification of the electron beam can be produced to provide information on electron energy, scan position and scan width.

The first step in the monitoring process is to qualify a representative sample of the products to be irradiated. This is done by irradiating a representative sample of the product and obtaining a signature map for the absorbed dose of that product. This signature map serves to inform the operator whether the product was adequately and uniformly penetrated and also serves as the qualification signature against which the signature maps of subsequently irradiated like products can be compared. The qualification signature is also examined to set the dose tolerance limits which are acceptable for particular points on the signature. Once the product has been qualified, irradiation of a quantity of like product can commence. A signature map for the absorbed dose of each product is produced and compared to the qualification signature. The comparison can be conducted by digitally comparing all of the points on the signatures. Alternative means of conducting the comparison include comparing minimum dose levels or comparing a selected quantity of points. If the differences between the qualification signature and the signature map for the product do not fall within predetermined tolerance limits, an alarm is triggered to notify the service centre operator who can then determine what the problem is and correct it.

The above monitoring process can optionally be conducted by comparing signature maps which display the collected charge for a product or by comparing the data used in their preparation. Once the dose level required for a product has been ascertained, the collected charge corresponding to that dose level can be determined by applying the correlation of collected charge to absorbed dose described above. A signature map displaying collected charge for a product can then be compared to a qualification signature of collected charge for a sample of that product to ascertain whether the required dose level has been achieved.

A print out of the signature map of each product is useful as a quality assurance record. The signature maps could be included with the product to satisfy the end user of the product that it has been adequately irradiated. The signature maps could also be used as an accurate and convenient form of quality assurance record for audits which are routinely conducted by regulatory authorities.

Other information not directly related to monitoring irradiation of a product can be read from the signature maps; for example, the speed of the conveyor and the dimensions of the product packages.

We claim:

1. A method for determining absorbed dose of a product disposed in the path of an electron beam comprising:

providing an electron beam source;

providing an electron beam stop in the path of said beam effective to absorb electrons incident thereon and generate an output proportional to the collected charge induced therein by said incident electrons;

placing said product in the path of said electron beam between said source and said beam stop;

measuring the collected charge in said beam stop; and correlating said measured collected charge to absorbed dose.

2. The method of claim 1 wherein the step of correlating the measured collected charge to the absorbed dose comprises:

obtaining charge deposition distribution values as a function of depth of a sample of said product;

obtaining dose deposition distribution values as a function of depth of said sample;

integrating said charge and dose deposition distribution values over the maximum depth of the product through which said beam can pass to obtain integrated charge deposition values and absorbed dose deposition values respectively;

subtracting said integrated charge deposition values from the total charge induced in said beam stop per incident electron in the absence of said product to obtain collected charge in said beam stop as a function of depth of said sample;

correlating said absorbed dose deposition values as a function of said collected charge distribution values;

obtaining from said correlation the absorbed dose deposition value associated with the measured collected charge.

3. A method for determining whether a product irradiated by an electron beam has acquired a predetermined absorbed dose comprising:

determining absorbed dose of the product in accordance with the method of claim 1 or 2;

comparing said determined absorbed dose to said predetermined absorbed dose; and rejecting said product if said determined absorbed dose is less than said predetermined absorbed dose.

4. The method of claim 3 wherein the predetermined absorbed dose is the absorbed dose of an irradiated representative sample of said product determined in accordance with the method of claim 1.

5. A method for determining whether a product disposed in the path of an electron beam has absorbed a predetermined dose comprising:

providing an electron beam source;

providing an electron beam stop in the path of said beam effective to absorb electrons incident thereon and generate an output proportional to the collected charge induced therein by said incident electrons;

determining the collected charge induced in said beam stop when a sample of said product has absorbed said predetermined dose;

placing said product in the path of said electron beam between said source and said beam stop;

measuring the collected charge in said beam stop; and rejecting said product if said measured collected charge exceeds said determined collected charge.

6. The method of claim 5 wherein the step of determining the collected charge induced in said beam stop when a sample of said product has absorbed said predetermined dose comprises:

obtaining dose deposition distribution values as a function of depth of said sample;

integrating said charge and dose deposition distribution values over the maximum depth of the product through which said beam can pass to obtain integrated charge deposition values and absorbed dose deposition values respectively;

subtracting said integrated charge deposition values from the total charge induced in said beam stop per incident electron in the absence of said product to obtain collected charge in said beam stop as a function of depth of said sample;

correlating said absorbed dose deposition values as a function of said collected charge distribution values;

obtaining from said correlation the collected charge value associated with the predetermined absorbed dose.

7. A method for monitoring the absorbed dose of a product moving through a scanned electron beam at right angles to said scanned electron beam as a function of time and beam position comprising;

providing an electron beam source;

providing an electron beam stop in the path of said beam effective to absorb electrons incident thereon and generate an output proportional to the collected charge induced therein by said incident electrons;

moving a representative sample of said product through the path of said electron beam between said source and said beam stop;

measuring the collected charge in said beam stop for said representative sample at predetermined values of time and beam position;

correlating said measured collected charge for said representative sample to absorbed dose for said representative sample to determine absorbed dose of said representative sample as a function of time and beam position;

moving said product through the path of said scanned electron beam;

measuring the collected charge in said beam stop at predetermined values of time and beam position for said product;

correlating said measured collected charge for said product to absorbed dose for said product to determine absorbed dose as a function of time and beam position;

comparing the absorbed dose as a function of time and beam position for said representative sample to the absorbed dose as a function of time and beam position for said product to determine the presence of predetermined levels of difference therebetween.

* * * * *